United States Patent [19]

Denis et al.

[11] Patent Number: 5,686,623

[45] Date of Patent: Nov. 11, 1997

[54] METHOD FOR PREPARING TAXANE DERIVATIVES

[75] Inventors: Jean-Noel Denis; Andrew-Elliot Greene, both of Uriage; Alice Kanazawa, Grenoble, all of France

[73] Assignee: Rhone-Poulenc Rorer, S.A., Antony, France

[21] Appl. No.: 424,386

[22] PCT Filed: Oct. 28, 1993

[86] PCT No.: PCT/FR93/01058

§ 371 Date: Apr. 28, 1995

§ 102(e) Date: Apr. 28, 1995

[87] PCT Pub. No.: WO94/10169

PCT Pub. Date: May 11, 1994

[30] Foreign Application Priority Data

Oct. 30, 1992 [FR] France ............ 92 13000

[51] Int. Cl.⁶ ............ C07D 413/12; C07D 305/14; C07D 263/04
[52] U.S. Cl. ............ 548/215; 544/172; 544/369; 544/209
[58] Field of Search ............ 548/215

[56] References Cited

FOREIGN PATENT DOCUMENTS

WO92/09589  6/1992  WIPO .

OTHER PUBLICATIONS

Tetrahedron Letters, vol. 33, No. 36, 1 Sep. 1992, Oxford, GB pp. 5185–5188, A. Commercon et al.

*Primary Examiner*—Johann Richter
*Assistant Examiner*—Laura L. Stockton
*Attorney, Agent, or Firm*—Finnegan, Henderson, Farabow, Garrett & Dunner, L.L.P.

[57] ABSTRACT

A method for preparing taxane derivatives of general formula (I) by esterifying protected baccatin III or protected 10-deacetyl baccatin III with an acid of general formula (II). In general formulae (I) and (II), Ar is an aryl radical; $R_1$ and $R_2$ which are the same or different, are a hydrogen atom, an alkyl, phenylalkyl, phenyl, alkoxyphenyl or dialkoxyphenyl radical, or $R_1$ or $R_2$, together with the carbon atom to which they are attached, form a 4–7 membered ring; $R_3$ is an acetyl radical or a hydroxy function protective grouping, and $R_4$ is a hydroxy function protective grouping; R is a phenyl radical or a radical of formula $R_5$—O— wherein $R_5$— is an alkyl, alkenyl, alkynyl, cycloalkyl, cycloalkenyl, phenyl or saturated or unsaturated nitrogenous heterocylcyl radical. The products of general formula (I) are particularly useful for preparing taxol, Taxotere and analogues thereof having remarkable antitumor properties.

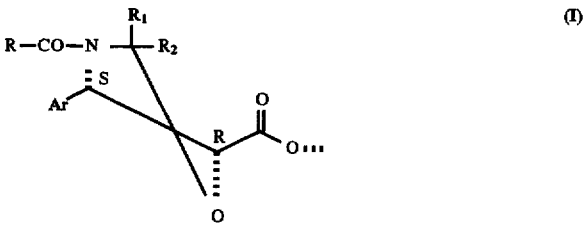

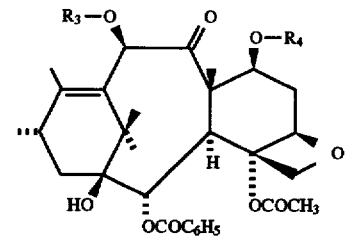

15 Claims, No Drawings

METHOD FOR PREPARING TAXANE DERIVATIVES

This application is a 371 of PCT/FR93/01058 filed Oct. 28, 1993.

DESCRIPTION OF THE INVENTION

The present invention relates to a process for the preparation of taxane derivatives of general formula:

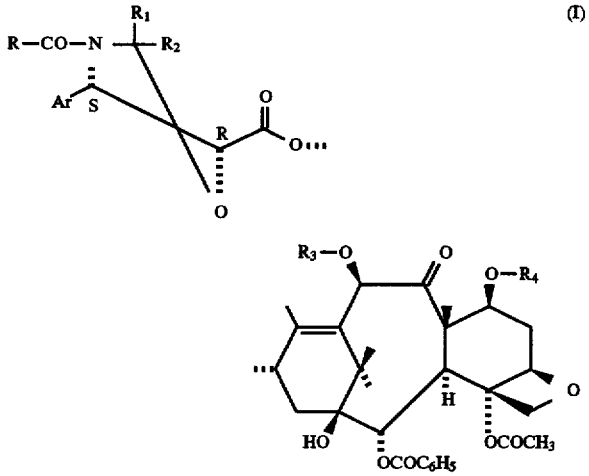

which are particularly advantageous intermediates for preparing taxol, Taxotere and their analogues which have notable antileukaemic and antitumour properties.

In the general formula (I),

Ar represents an aryl radical,

R represents the phenyl radical or a radical $R_5$—O— which $R_5$ represents a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals optionally being substituted by one or a number of substituents chosen from the halogen atoms and the hydroxyl radical, alkoxy radical containing 1 to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl cyano radical, carboxyl radical or alkoxycarbonyl radical, the alkyl part of which contains 1 to 4 carbon atoms, or a phenyl radical optionally substituted by one or a number of atoms or radicals chosen from the halogen atoms and the alkyl radicals containing 1 to 4 carbon atoms or the alkoxy radicals containing 1 to 4 carbon atoms, a saturated or unsaturated nitrogen-containing heterocyclyl radical containing 4 to 6 members and optionally substituted by one or a number of alkyl radicals containing 1 to 4 carbon atoms, it being understood that the cycloalkyl, cycloalkenyl or bicycloalkyl radicals may optionally be substituted by one or a number of alkyl radicals containing 1 to 4 carbon atoms, $R_1$ and $R_2$, which are identical or different, represent a hydrogen atom or an alkyl, phenylalkyl, phenyl, alkoxyphenyl or dialkoxyphenyl radical or else $R_1$ and $R_2$ form, together with the carbon atom to which they are bonded, a ring having from 4 to 7 members, $R_3$ represents an acetyl radical or a protective group of the hydroxyl functional group and $R_4$ represents a protective group of the hydroxyl functional group.

More particularly, Ar represents a phenyl or α- or β-naphthyl radical optionally substituted by one or a number of atoms or radicals, identical or different, chosen from the halogen atoms (fluorine, chlorine, bromine, iodine) and the alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, that the alkenyl and alkynyl radicals contain 3 to 8 carbon atoms and that the aryl radicals are phenyl or α- or β-naphthyl radicals, or else Ar represents an aromatic heterocyclic radical having 5 members and containing one or a number of atoms, identical or different, chosen from the nitrogen, oxygen or sulphur atoms, optionally substituted by one or a number of substituents, identical or different, chosen from the halogen atoms (fluorine, chlorine, bromine, iodine) and the alkyl radicals containing 1 to 4 carbon atoms, aryl radicals containing 6 to 10 carbon atoms, alkoxy radical containing 1 to 4 carbon atoms, aryloxy radical containing 6 to 10 carbon atoms, amino radical, alkylamino radical containing 1 to 4 carbon atoms, dialkylamino radical, in which each alkyl part contains 1 to 4 carbon atoms, acylamino radical, the acyl part of which contains 1 to 4 carbon atoms, alkoxycarbonylamino radical containing 1 to 4 carbon atoms, acyl radical containing 1 to 4 carbon atoms, arylcarbonyl, the aryl part of which contains 6 to 10 carbon atoms, cyano radical, carboxyl radical, carbamoyl radical, alkylcarbamoyl radical, the alkyl part of which contains 1 to 4 carbon atoms, dialkylcarbamoyl radical, each alkyl part of which contains 1 to 4 carbon atoms, or alkoxycarbonyl radical, the alkoxy part of which contains 1 to 4 carbon atoms.

More particularly, Ar represents a phenyl, 2- or 3-thienyl or 2- or 3-furyl radical optionally substituted by one or a number of atoms or radicals, which are identical or different, chosen from the halogen atoms and the alkyl, alkoxy, amino, dialkylamino, acylamino, alkoxycarbonylamino and trifluoromethyl radicals.

More particularly still, Ar represents a phenyl radical optionally substituted by a chlorine or fluorine atom or by an alkyl (methyl), alkoxy (methoxy), dialkylamino (dimethylamino), acylamino (acetylamino) or alkoxycarbonylamino (t-butoxycarbonylamino) or 2- or 3-thienyl or 2- or 3-furyl radical.

More particularly, $R_3$ represents an acetyl radical or a protective group of the hydroxyl functional group chosen from the (2,2,2-trichloroethoxy)carbonyl, (2-trichloromethylisopropoxy)carbonyl, trialkylsilyl, dialkylarylsilyl, alkyldiarylsilyl or triarylsilyl radicals in which the alkyl radicals contain 1 to 4 carbon atoms and the aryl radicals are, preferably, phenyl radicals and $R_4$ represents a protective group of the hydroxyl functional group chosen from the (2,2,2-trichloroethoxy)carbonyl, (2-trichloromethylisopropoxy)carbonyl, benzyl, 4-methoxybenzyl, 2,4-dimethoxybenzyl, trialkylsilyl, dialkylarylsilyl, alkyldiarylsilyl or triarylsilyl radicals in which the alkyl radicals contain 1 to 4 carbon atoms and the aryl radicals are, preferably, phenyl radicals.

A description is given in International Application PCT WO 9209589 of the preparation of the products of general formula (I) by esterification of protected baccatin III or protected 10-deacetylbaccatin III of general formula:

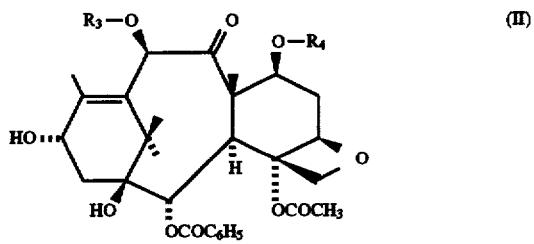

in which $R_3$ and $R_4$ are defined as above, by means of an acid of general formula:

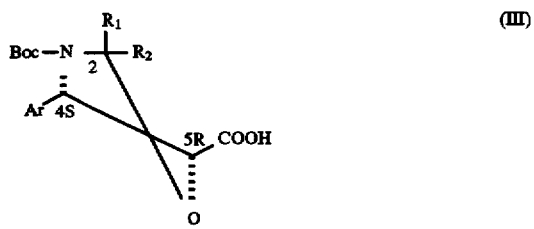

in which Ar, $R_1$ and $R_2$ are defined as above and Boc represents the t-butoxycarbonyl radical, and of their conversion to taxol, Taxotere or their derivatives of general formula:

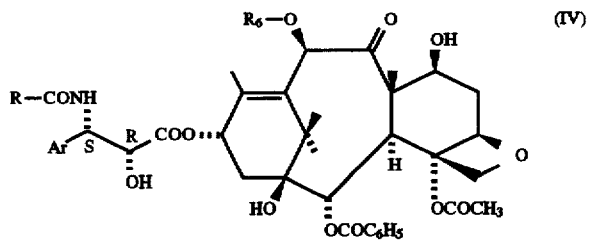

in which Ar is defined as above, $R_6$ represents a hydrogen atom or the acetyl radical and R represents the phenyl radical or a radical $R_5$—O— which $R_5$ is defined as above, by passing through the intermediacy of a product of general formula:

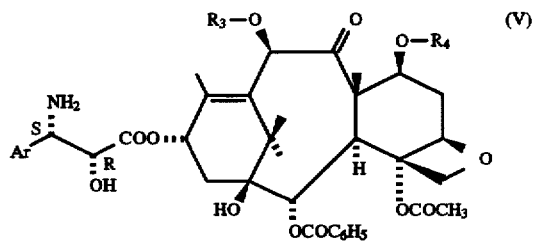

in which $R_3$ and $R_4$ are defined as above.

According to the previously known processes, it was necessary, to obtain the products of general formula (IV), in which the absolute configuration of the side chain is necessary for the antitumoral activity, to use the acid of general formula (III) in which the carbon atoms in the 4- and 5-positions respectively have the S and R configurations.

It has now been found, and it is this which forms the subject of the present invention, that the products of general formula (I) can be obtained, with a stereoselectivity in the region of 100%, by esterification of protected baccatin III or protected 10-deacetylbaccatin III by means of an acid of general formula:

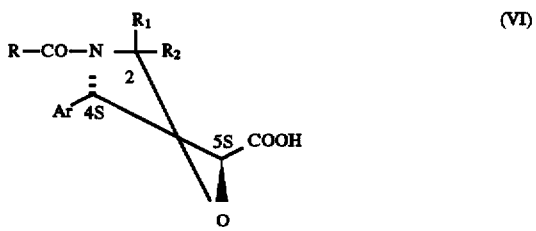

in which Ar, R, $R_1$ and $R_2$ are defined as above and in which the carbon atoms in the 4- and 5-positions each have the S configuration, or of an activated derivative of this acid.

The process according to the invention makes it possible to stereoselectively obtain the product of general formula (I) from an acid of general formula (VI), optionally mixed with an acid of general formula (III).

According to the present invention, the esterification of protected baccatin III or protected 10-deacetylbaccatin III by the acid of general formula (VI) is carried out in the presence of a condensation agent such as an imide, such as dicyclohexyl-carbodiimide, or a reactive carbonate, such as di-2-pyridyl ketone, and of an activating agent such as an aminopyridine, such as 4-dimethylaminopyridine or 4-pyrrolidinopyridine, the reaction being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 0° and 90° C.

The esterification can also be carried out by using the acid of general formula (VI) in the anhydride form of general formula:

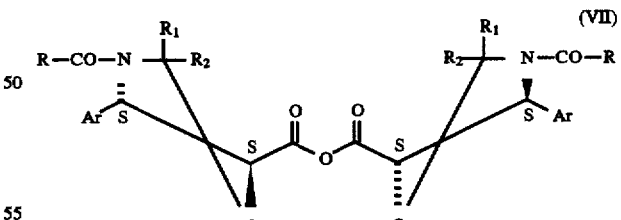

in which Ar, R, $R_1$ and $R_2$ are defined as above, in the presence of an activating agent such as an aminopyridine, such as 4-dimethylaminopyridine or 4-pyrrolidinopyridine, the reaction being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 0° and 90° C.

The esterification can also be carried out by using the acid of general formula (VI) in the halide or mixed anhydride form of general formula:

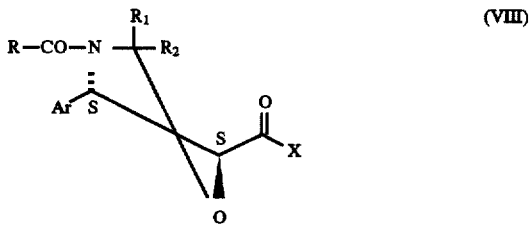
(VIII)

in which Ar, R, $R_1$ and $R_2$ are defined as above and X represents a halogen atom or an acyloxy or aroyloxy radical, optionally prepared in situ, in the presence of a base which is preferably a nitrogenous organic base such as a tertiary aliphatic amine, a pyridine or an aminopyridine, such as 4-dimethylaminopyridine or 4-pyrrolidinopyridine, the reaction being carried out in an inert organic solvent chosen from ethers such as tetrahydrofuran, diisopropyl ether, methyl t-butyl ether or dioxane, ketones such as methyl t-butyl ketone, esters such as ethyl acetate, isopropyl acetate or n-butyl acetate, nitriles such as acetonitrile, aliphatic hydrocarbons such as pentans, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 0° and 90° C.

The acid of general formula (VI) can be obtained by saponification of the ester of general formula

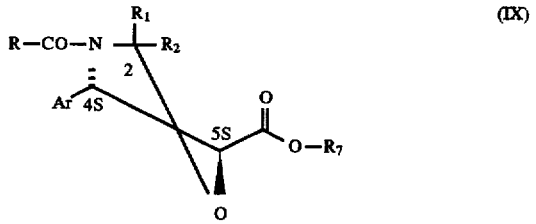
(IX)

in which Ar, R, $R_1$ and $R_2$ are defined as above and $R_7$ represents an alkyl radical containing 1 to 4 carbon atoms optionally substituted by one or a number of phenyl radicals.

Generally, the saponification is carried out in aqueous medium, optionally in the presence of an aliphatic alcohol containing 1 to 4 carbon atoms (methanol, ethanol, isopropanol, t-butanol), in the presence of an inorganic base chosen from hydroxides, carbonates or bicarbonates of alkali metals or alkaline-earth metals, at a temperature between 0° and 50° C., preferably in the region of 20° C.

The ester of general formula (IX) can be obtained by reacting an aldehyde or a ketone of general formula:

(X)

in which $R_1$ and $R_2$ are defined as above, optionally in the form of a dialkyl acetal or of an enol alkyl ether, with an ester of general formula:

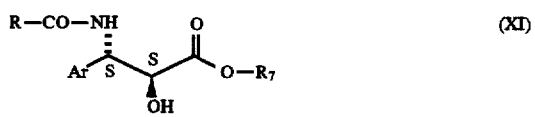
(XI)

in which Ar, R and $R_7$ are defined as above, the reaction being carried out in an inert organic solvent in the presence of a strong inorganic acid, such as sulphuric acid, or a strong organic acid, such as p-toluenesulphonic acid, optionally in the pyridinium salt form, at a temperature between 0° and the boiling temperature of the reaction mixture. Solvents which are particularly well suited are aromatic hydrocarbons such as toluene.

The ester of general formula (XI) can be obtained by reacting benzoyl chloride or a product of general formula $R_5$—O—CO—Y, in which $R_5$ is defined as above and Y represents a halogen atom or a radical —O—$R_5$ or —O—CO—$R_5$, with an ester of general formula:

(XII)

in which Ar and $R_7$ are defined as above, the reaction being carried out in an organic solvent such as an aliphatic ester, such as ethyl acetate, or a halogenated aliphatic hydrocarbon such as dichloromethane, optionally in the presence of an inorganic base such as sodium bicarbonate or an organic base such as triethylamine. Generally, the reaction is carried out at a temperature between 0° and 50° C., preferably in the region of 20° C.

The ester of general formula (XII) can be obtained according to the process described by E. Kamandi et al., Arch. Pharmaz., 308, 135–141 (1975).

The anhydride of general formula (VII) can be obtained by reacting a dehydrating agent such as dicyclohexylcarbodiimide with the acid of general formula (VI), the reaction being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 0° and 30° C.

The activated acid of general formula (VIII) can be obtained by reacting a sulphuryl halide, preferably the chloride, or a product of general formula:

$R_8$—CO—Z (XIII)

in which $R_8$ represents an alkyl radical containing 1 to 4 carbon atoms or a phenyl radical optionally substituted by 1 to 5 atoms or radicals, which are identical or different, chosen from the halogen atoms and the nitro, methyl or methoxy radicals and Z represents a halogen atom, preferably a chlorine atom, with an acid of general formula (VI), the reaction being carried out in a suitable organic solvent, such as tetrahydrofuran, in the presence of an organic base such as a tertiary amine, such as triethylamine, at a temperature between 0° and 30° C.

The acid of general formula (VI) can also be obtained by oxidation of a product of general formula:

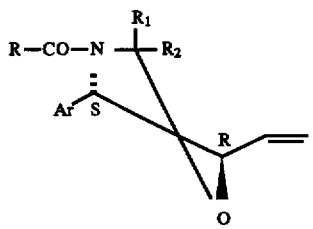

in which Ar, R, R$_1$ and R$_2$ are defined as above.

Generally, the oxidation is carried out by means of an alkali metal periodate (sodium periodate), in the presence of a catalytic amount of a ruthenium salt (RuCl$_3$) and of sodium bicarbonate, the reaction being carried out in aqueous/ organic medium such as, for example, an acetonitrile/carbon tetrachloride/water mixture. Generally, the reaction is carried out at a temperature in the region of 20° C.

The product of general formula (XIV) can be obtained by reacting an aldehyde or a ketone of general formula (X), optionally in the form of a dialkyl acetal or of an enol ester, with a product of general formula:

in which Ar and R are defined as above, the reaction being carried out in an inert organic solvent in the presence of a strong inorganic acid, such as sulphuric acid, or a strong organic acid, such as p-toluenesulphonic acid, optionally in the pyridinium salt form, at a temperature between 0° C. and the boiling temperature of the reaction mixture. Solvents which are particularly well suited are aromatic hydrocarbons.

The product of general formula (XV) can be obtained under the conditions described in EP-A-0,530,385.

The ester of general formula (IX), in which Ar and R$_7$ are defined as above, R$_1$ represents a hydrogen atom and R$_2$ represents a phenyl, alkoxyphenyl or dialkoxyphenyl radical, can also be obtained by cyclization of a product of general formula:

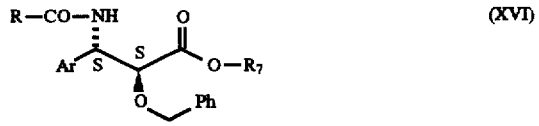

in which Ar, R and R$_7$ are defined as above and Ph represents a phenyl, alkoxyphenyl or dialkoxyphenyl radical, the reaction preferably being carried out in anhydrous medium, in an organic solvent chosen from ethers, esters, ketones, nitriles, optionally halogenated aliphatic hydrocarbons and optionally halogenated aromatic hydrocarbons in the presence of an oxidizing agent such as dichlorodicyanobenzoquinone at a temperature between 0° C. and the boiling temperature of the reaction mixture. The reaction is preferably carried out in an halogenated aliphatic hydrocarbon, such as dichloromethane, or acetonitrile at a temperature in the region of 20° C.

The cyclization leads to the formation of a mixture of 2R and 2S epimers of the product of general formula (IX) which can be separated according to the usual methods. It is particularly advantageous to preferentially obtain the 2R epimer in order to prepare taxol, Taxotere or their derivatives from a product of general formula (I).

The invention also relates to the acids of general formula (VI), optionally in the salt, ester, anhydride, mixed anhydride or halide form.

The taxane derivatives of general formula (I) obtained by the use of the process according to the invention can be converted to taxol, Taxotere or their analogues according to the processes described in International Application PCT WO 9209589, when R$_1$ and R$_2$ each represent an alkyl or phenylalkyl radical by passing through the intermediacy of the product of general formula (V) or else by treatment in acid medium (hydrochloric acid, sulphuric acid, acetic acid, methanesulphonic acid, trifluoromethanesulphonic acid, p-toluenesulphonic acid), the reaction being carried out in an organic solvent (alcohol, ether, ester, aliphatic hydrocarbon, halogenated aliphatic hydrocarbon, aromatic hydrocarbon, nitrile) at a temperature between −10° and 60° C., or, when R$_1$ represents a hydrogen atom and R$_2$ represents a phenyl, alkoxyphenyl or dialkoxyphenyl radical, by passing through the intermediacy of a product of general formula

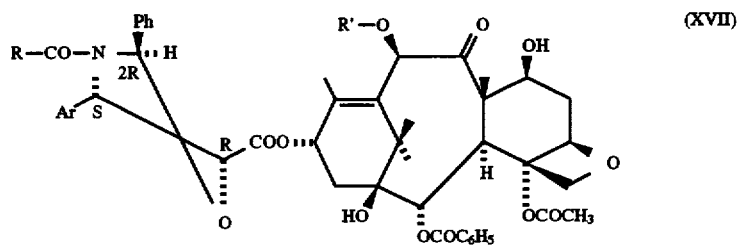

in which Ar, R and Ph are defined as above and R' represents a hydrogen atom or the acetyl radical, after replacement of the protective groups R$_4$ and optionally R$_3$ by hydrogen atoms according to known methods.

EXAMPLES

The following examples illustrate the present invention.

Example 1

28 mg (0.087 mmol) of (4S,5S)-3-t-butoxy-carbonyl-2,2-dimethyl-4-phenyl-1,3-oxazolidine-5-carboxylic acid, in solution in 1.5 cm$^3$ of anhydrous toluene, are put, under an argon atmosphere, into a 10 cm$^3$ round-bottomed flask equipped with a magnetic stirrer system. 18 mg (0.087 mmol) of distilled dicyclohexylcarbodiimide are then added. The mixture is left to react for 5 minutes at a temperature in the region of 20° C. and then, in a single step, a mixture of 3.5 mg (0.029 mmol) of 4-(N,N-dimethylamino)pyridine and 26 mg (0.029 mmol) of 4-acetoxy-2α-benzoyloxy-5β,-20-epoxy-1,13α-dihydroxy-9-oxo-7β,10β-bis(2,2,2-trichloroethoxycarbonyloxy)-11-taxene is added. The mixture is left to react for 5 minutes at a temperature in the region of 20° C. and then is heated for 16 hours at 72° C. After cooling to a temperature in the region of 20° C., 40 cm$^3$ of ethyl acetate are added. The organic phase is washed with 5 cm³ of distilled water, 2 times 5 cm³ of a saturated aqueous sodium hydrogencarbonate solution and then with 5 cm³ of a saturated aqueous sodium chloride solution and finally dried over anhydrous sodium sulphate. After filtration and evaporation of the solvents under reduced pressure, a residue (solid) is obtained which is purified by preparative silica thin layer chromatography, eluting with an ether/hexane/ dichloromethane (5/20/75 by volume) mixture. There are thus obtained, with a yield of 86%, 30 mg (0.025 mmol) of 4-acetoxy-2α-benzoyloxy-5β,20-epoxy-1-hydroxy-9-oxo-7β,10β-bis(2,2,2-trichloro-ethoxycarbonyl)oxy-11-taxen-13α-yl (4S,5R)-3-t-butoxy-carbonyl-2,2-dimethyl-4-phenyl-1,3-oxazolidine-5-carboxylate, the characteristics of which are the following:

infrared spectrum (film): main characteristic absorption bands at 3450, 2970, 2910, 1760, 1720, 1700, 1600, 1580, 1450, 1375, 1360, 1245, 1170, 1135, 1100, 1080, 1060, 1020, 995, 975, 960, 900, 820, 765 and 720 cm⁻¹ proton nuclear magnetic resonance spectrum (300 MHz, CDCl₃, chemical shifts in ppm, coupling constants J in Hz): 1.18 (s, 12H), 1.27 (s, 3H), 1.6–2.0 (m, 1H), 1.76 (s, 3H), 1.81 (s, 3H), 1.83 (s, 3H), 1.95 (s, 3H), 2.05 (s, 3H), 2.20 (d, J=9, 2H), 2.55–2.65 (m, 1H), 3.90 (d, J=7, 1H), 4.20 (AB$_q$, J$_{AB}$=8.5, δ$_A$–δ$_B$=47.2, 2H), 4.47 (d, J=6.4, 1H), 4.75 (AB$_q$, J$_{AB}$=12, δ$_A$–δ$_B$=92.2, 2H), 4.78 (s, 2H), 4.91 (d, J=12, 1H), 5.12 (broad s, 1H), 5.58 (dd, J=7.1 and 10.6, 1H), 5.67 (d, J=7, 1H), 6.25 (s, 1H), 6.28 (t, J=9, 1H), 7.2–7.4 (m, 5H, aromatic protons), 7.47–7.52 (m, 2H, aromatic protons), 7.61–7.66 (m, 1H, aromatic proton), 8.03–8.05 (m, 2H, aromatic protons)

mass spectrum (FAB(+)-NBA matrix): molecular ion (large): M⁺ (1198).

(4S,5S)-3-t-Butoxycarbonyl-2,2-dimethyl-4-phenyl-1,3-oxazolidine-5-carboxylic acid can be prepared in the following way:

40 mg (0.12 mmol) of (4S,5S)-3-t-butoxycarbonyl-2,2-dimethyl-4-phenyl-5-methoxycarbonyl-1,3-oxazolidine, 5 cm³ of methanol, 2 cm³ of distilled water and 50 mg (0.36 mmol) of solid potassium carbonate are introduced successively into a 25 cm³ round-bottomed flask equipped with a magnetic stirrer system. The reaction mixture is stirred for 40 hours at a temperature in the region of 20° C. and then the methanol is evaporated under reduced pressure. 13 cm³ of water are added and the aqueous phase obtained is then washed 3 times with 20 cm³ of ethyl ether. The basic aqueous phase is cooled to 0° C. and is then acidified, in the presence of 20 cm³ of dichloromethane and with vigorous stirring, by addition of a 2M aqueous hydrochloric acid solution. The organic phase is separated by settling and the aqueous phase is then extracted 6 times with 30 cm³ of dichloromethane. The combined organic phases are washed 3 times with 5 cm³ of distilled water, then once with 5 cm³ of a saturated aqueous sodium chloride solution and then finally dried over anhydrous magnesium sulphate. After filtration and concentration to dryness under reduced pressure, there are obtained, with a yield of 99%, 38 mg (0.12 mmol) of (4S,5S)-3-t-butoxy-carbonyl-2,2-dimethyl-4-phenyl-1,3-oxazolidine-5-carboxylic acid, the characteristics of which are the following:

infrared spectrum (film): main characteristic absorption bands at 3650–2200, 2970, 2920, 1760, 1740, 1700, 1470, 1450, 1370, 1250, 1215, 1165, 1135, 1110, 1065, 875 and 690 cm⁻¹ proton nuclear magnetic resonance spectrum (200 MHz, CDCl₃, chemical shifts in ppm, coupling constants J in Hz): 1.20 (maj) and 1.43 (min) (2 broad s, 9H), 1.64 (s, 3H), 1.94 (s, 3H), 3.0 (very broad s, 1H), 4.97 (distorted d, J=7, 1H), 5–5.25 (m, 1H), 7.2–7.4 (m, 5H, aromatic protons)

mass spectrum (C.I., NH₃+isobutane): 339 (MH⁺), 322 (MH⁺—OH), 283, 266, 222, 206, 158, 124, 110.

(4S,5S)-3-t-Butoxycarbonyl-2,2-dimethyl-4-phenyl-5-methoxycarbonyl-1,3-oxazolidine can be prepared in the following way:

147.5 mg (0.50 mmol) of methyl (2S,3S)-3-t-butoxycarbonylamino-3-phenyl-2-hydroxypropionate and 2.5 cm³ of anhydrous toluene are introduced, under an argon atmosphere, into a 10 cm³ round-bottomed flask equipped with a magnetic stirrer system. 10 grains of 4 Å molecular sieve, 188.5 µl (144.2 mg, 2.0 mmol) of 2-methoxypropene and 12.5 mg (0.05 mmol) of pyridinium p-toluenesulphonate are then added to the suspension obtained. The mixture is allowed to react for 1 hour at a temperature in the region of 20° C. and is then heated to 120° C. and allowed to react at this temperature for 2 hours. The resulting dark-brown reaction mixture is cooled to a temperature in the region of 20° C. 60 cm³ of dichloromethane are added. The organic phase is washed with 5 cm³ of a saturated aqueous sodium hydrogen-carbonate solution, 3 times with 5 cm³ of water and then once with 5 cm³ of a saturated aqueous sodium chloride solution. The organic phase is dried over anhydrous sodium sulphate. After filtration and concentration to dryness under reduced pressure, a residue is obtained which is chromatographed on a column of silica gel, eluting with an ethyl ether/hexane (15/85 by volume) mixture. There are obtained, with a yield of 36%, 60 mg (0.18 mmol) of (4S,5S)-3-t-butoxycarbonyl-2,2-dimethyl-4-phenyl-5-methoxycarbonyl-1,3-oxazolidine, the characteristics of which are the following:

infrared spectrum (film): main characteristic absorption bands at 3060, 3025, 2975, 2920, 1775, 1740, 700, 1490, 1480, 1450, 1440, 1365, 1250, 1210, 1165, 1110, 1070, 1050, 1030, 890, 760, 720 and 695 cm⁻¹ proton nuclear magnetic resonance spectrum (200 MHz, CDCl₃, chemical shifts in ppm, coupling constants J in Hz): 1.20 (maj) and 1.43 (min) (2 broad s, 9H), 1.63 (s, 3H), 1.90 (min) and 1.95 (maj) (2 broad s, 3H), 3.32 (s, 3H), 4.95–5.20 (m, 1H), 4.97 (distorted d, J=7, 1H), 7.15–7.40 (m, 5H, aromatic protons)

mass spectrum (C.I., NH₃+isobutane): 353 (M+NH₄⁺), 336 (MH⁺), 320 (M⁺—CH₃), 297, 280, 239, 236, 222, 220.

Methyl (2S,3S)-3-t-butoxycarbonylamino-3-phenyl-2-hydroxypropionate can be prepared in the following way:

A 4N aqueous sodium hydroxide solution is added, over 5 minutes, to a suspension of 6.5 g of α-methylbenzylamine (2S,3R)-phenylglycidate in 20 cm³ of toluene and 10 cm³ of water. After stirring for 2 hours at a temperature in the region of 20° C., the separated aqueous phase is extracted with 2 times 7 cm³ of toluene. The aqueous phase is introduced into an autoclave. After having added 97.5 cm³ of a 32% (w/v) aqueous ammonia solution and 1.22 g of ammonium chloride, the autoclave is closed and then heated, with stirring, for 6 hours at 60° C. (autogenous pressure of 3 bar). After cooling to a temperature in the region of 20° C., 6 cm³ of a 4N aqueous sodium hydroxide solution are added. The mixture is stirred for 30 minutes, the ammonia is removed under reduced pressure and then the mixture is concentrated to dryness under reduced pressure (45 mm of mercury, 6 kPa) at 45° C. The residue obtained is taken up in 75 cm³ of methanol. A methanolic sulphuric acid solution consisting of 4.83 g of concentrated sulphuric acid in 20 cm³ of methanol is added over 35 minutes at 20° C. to the suspension obtained. The reaction mixture is heated at 50° C. for 3 hours 30 minutes. After cooling to 0° C., a solution of 27 g of sodium carbonate in 20 cm³ of water is added. After evolution of carbon dioxide has ceased, the reaction mixture is cooled to 23° C. over 30 minutes. A solution of 6.1 g of di-t-butyl dicarbonate in 7 cm³ of methanol is then added over 30 minutes. The mixture is stirred for 4 hours and then, after evaporation of 50 cm³ of methanol, 60 cm³ of water are added and then all the methanol is evaporated. The product which precipitates is separated by filtration, washed with 2 times 25 cm³ of water and dried to constant weight. There are thus obtained, with a yield of 30%, 2 g of methyl (2S,3S)-3-t-butoxycarbonylamino-3-phenyl-2-hydroxypropionate, the characteristics of which are the following:

melting point: 135.5°–136° C.

optical rotation: $[\alpha]_D^{25}=+29.6°$ (c=0.5, chloroform)

infrared spectrum (film): main characteristic absorption bands at 3380, 3350, 3000, 2970, 2930, 1720, 1690, 1510, 1435, 1385, 1360, 1310, 1285, 1230, 1205, 1170, 1105, 1005, 860, 770, 750, 730 and 690 cm$^{-1}$ proton nuclear magnetic resonance spectrum (200 MHz, CDCl$_3$, chemical shifts in ppm, coupling constants J in Hz): 1.43 (s, 9H), 2.84 (d, J=7, 1H), 3.71 (s, 3H), 4.60 (dd, J=3.5 and 7, 1H), 5.10 (distorted d, J=8, 1H), 7.20–7.37 (m, 5H, aromatic protons)

proton nuclear magnetic resonance spectrum (360 MHz, d$_6$-DMSO, 298° K., chemical shifts in ppm, coupling constants J in Hz): 1.31 (broad s, 9H), 3.55 (s, 3H), 4.14 (d, J=7.7, 1H), 4.71 (dd, 1H), 5.65 (broad s, 1H), 7.18 (d, J=7, 1H), 7.15–7.3 (m, 5H).

EXAMPLE 2

9 mg (0.028 mmol) of (4S,5S)-3-benzoyl-2,2-dimethyl-4-phenyl-1,3-oxazolidine-5-carboxylic acid, in solution in 0.46 cm³ of anhydrous toluene, are put into a 5 cm³ single-necked, round-bottomed flask equipped with a magnetic stirrer system. 5.7 mg (0.028 mmol) of dicyclohexylcarbodiimide are then added. The reaction mixture, which has become cloudy, is allowed to react for 5 minutes at a temperature in the region of 20° C. and then a mixture of 6.4 mg (0.009 mmol) of 4,10β-diacetoxy-2α-benzoyloxy-5β,20-epoxy-1,13α-dihydroxy-9-oxo-7β-triethylsilyloxy-11-taxene and 1.1 mg (0.009 mmol) of 4-(N,N-dimethylamino) pyridine is added. The reaction mixture is allowed to react for 5 minutes at a temperature in the region of 20° C. and is then heated for 16 hours at 72° C.

After cooling to a temperature in the region of 20° C., the reaction mixture is diluted by addition of 40 cm³ of ethyl acetate. The organic phase is washed with 2 times 5 cm³ of a saturated aqueous sodium bicarbonate solution, 3 times 5 cm³ of water, then once with 5 cm³ of a saturated aqueous sodium chloride solution and is finally dried over anhydrous sodium sulphate. After filtration and removal of the solvents under reduced pressure, the residue obtained (21 mg) is purified by silica thin layer chromatography, eluting with an ethyl ether/dichloromethane (8/92 by volume) mixture over two passes. There are thus obtained, with a yield of 91%, 8.4 mg (0.008 mmol) of 4,10β-diacetoxy-2α-benzoyloxy-5β,20-epoxy-1-hydroxy-9-oxo-7β-triethylsilyloxy-11-taxen-13α-yl (4S,5R)-3-benzoyl-2,2-dimethyl-4-phenyl-1,3-oxazolidine-5-carboxylate, the characteristics of which are the following:

infrared spectrum (film): main characteristic absorption bands at 3400, 2930, 2850, 1730, 1720, 1630, 1590, 1570, 1440, 1360, 1340, 1230, 1195, 1065, 1015, 1005, 980 and 810 cm$^{-1}$ proton nuclear magnetic resonance spectrum (400 MHz, CDCl$_3$, chemical shifts in ppm, coupling constants J in Hz): 0.54–0.61 (m, 6H), 0.92 (t, J=8, 9H), 1.20 (s, 3H), 1.22 (s, 3H), 1.65 (s, 3H), 1.86 (s, 3H), 1.93 (broad s, 3H), 2.00 (s, 3H), 2.08 (s, 3H), 2.19 (s, 3H), 1.82–2.15 (m, 3H), 2.46–2.54 (m, 1H), 3.77 (d, J=7.2, 1H), 4.16 (AB$_q$, J$_{AB}$=8.4, $\delta_A-\delta_B$=59.4, 2H), 4.46 (dd, J=6.6 and 10.5, 1H), 4.56 (d, J=6.8, 1H), 4.88 (d, J=8, 1H), 5.27 (d, J=6, 1H), 5.64 (d, J=7.2, 1H), 6.24 (t, J=9, 1H), 6.45 (s, 2H), 6.94 (broad s, 2H, aromatic protons), 7.11–7.26 (m, 8H, aromatic protons), 7.44–7.48 (m, 2H, aromatic protons), 7.59–7.61 (m, 1H, aromatic proton), 8.00–8.02 (m, 2H, aromatic protons)

$^{13}$C magnetic resonance spectrum (100 MHz, CDCl$_3$): 5.20, 6.69, 9.99, 14.26, 20.82, 21.07, 21.62, 26.42, 35.27, 37.04, 43.18, 46.69, 58.28, 65.97, 71.68, 72.06, 74.79, 74.85, 76.32, 78.93, 80.74, 84.09, 93.43, 102.65, 126.11, 126.86, 127.83, 128.02, 128.50, 128.69, 129.14, 129.43, 130.00, 133.67, 133.82, 138.81, 139.90, 166.93, 169.13, 169.85, 201.60 mass spectrum (FAB(+)-NBA matrix+KCl): 1046, 1008 (MH$^+$), 948, 930.

(4S,5S)-3-Benzoyl-2,2-dimethyl-4-phenyl-1,3-oxazolidine-5-carboxylic acid can be prepared in the following way:

12.5 mg (0.04 mmol) of (4S,5R)-5-vinyl-3-benzoyl-2,2-dimethyl-4-phenyl-1,3-oxazolidine, in solution in 80 µl of acetonitrile, are put into a 2 cm³ single-necked, round-bottomed flask equipped with a magnetic stirrer system. 80 µl of carbon tetrachloride, 120 µl of water and 22 mg (0.26 mmol) of pure sodium bicarbonate are then successively added. 47 mg (0.22 mmol) of sodium periodate are then added in small portions with vigorous stirring. The mixture is allowed to react for 5 minutes at a temperature in the region of 20° C. and then 2.4 mg of ruthenium trichloride are added in a single step. The resulting black heterogeneous mixture is stirred vigorously at 20° C. for 72 hours.

The reaction mixture is diluted in 10 cm³ of water. The basic organic phase obtained is washed with 3 times 10 cm³ of ether. The basic aqueous phase is cooled to 0° C. and is then acidified, with vigorous stirring and in the presence of 20 cm³ of dichloromethane, with a 2M aqueous hydrochloric acid solution to pH=1. After settling, the acidic aqueous phase is extracted with 6 times 15 cm³ of dichloromethane. The combined organic phases are washed 3 times with 5 cm³ of water and then once with 5 cm³ of a saturated aqueous sodium chloride solution. After drying over anhydrous soduium sulphate and filtration, the organic phase is concentrated to dryness under reduced pressure. There are thus obtained, with a yield of 77%, 10.0 mg (0.031 mmol) of (4S,5S)-3-benzoyl-2,2-dimethyl-4-phenyl-1,3-oxazolidine-5-carboxylic acid, the characteristics of which are the following:

infrared spectrum (film): main characteristic absorption bands at 3700–2300 2970, 2940, 2930, 2900, 2825, 1740, 1600, 1590, 1570, 1420–1400, 1370, 1360, 1190, 1180, 1150, 1120, 1090 and 855 cm$^{-1}$ proton nuclear magnetic resonance spectrum: (200 MHz, CDCl$_3$, chemical shifts in ppm): 1.81 (s, 3H), 2.11 (s, 3H), 4.90–5.06 (m, 2H), 6.78–6.93 (m, 4H, aromatic protons), 7.07–7.30 (m, 6H, aromatic protons).

(4S,5R)-5-Vinyl-3-benzoyl-2,2-dimethyl-4-phenyl-1,3-oxazolidine can be prepared in the following way:

32 mg (0.12 mmol) of (1S,2R)-1-phenyl-1-benzoylamino-2-hydroxy-3-butene, in suspension in 0.64 cm³ of anhydrous toluene, are put, under an argon atmosphere, in a 10 cm³ single-necked, round-bottomed flask equipped with a magnetic stirrer system and a reflux condenser. 226 μl (173 mg, 2.4 mmol) of 2-methoxypropene, 6.0 mg (0.024 mmol) of pyridinium p-toluenesulphonate and 8 grains of 4 Å molecular sieve are then added. The resulting reaction mixture is allowed to react at a temperature in the region of 15° C. for 2.5 hours and is then heated at 100° C. for 2 hours. After cooling to a temperature in the region of 15° C., the reaction mixture is diluted in 40 cm³ of dichloromethane. The organic phase is washed once with 5 cm³ of a saturated sodium bicarbonate solution, 3 times with 5 cm³ of water and once with a saturated aqueous sodium chloride solution and is then dried over anhydrous sodium sulphate. After filtration and concentration to dryness under reduced pressure, the residue obtained is purified by chromatography on silica gel, eluting a first time with an ethyl ether/dichloromethane (2/98 by volume) mixture and then a second time with an ethyl acetate/hexane (10/90 by volume) mixture. There are thus obtained, with a yield of 38%, 14 mg (0.0456 mmol) of (4S,5R)-5-vinyl-3-benzoyl-2,2-dimethyl-4-phenyl-1,3-oxazolidine, the characteristics of which are the following:

infrared spectrum (film): main characteristic absorption bands at 3050, 3010, 2980, 2920, 1635, 1595, 1570, 1490, 1385, 1370, 1355, 1245, 1215, 1145, 1065, 1030, 1020, 935, 850 and 690 cm$^{-1}$ proton nuclear magnetic resonance spectrum (400 MHz, CDCl$_3$, chemical shifts in ppm, coupling constants J in Hz): 1.78 (s, 3H), 2.01 (s, 3H), 4.59 (d, J=6.4, 1H), 4.79 (pst, J=6.4, 1H), 4.97–5.10 (m, 2H), 5.21–5.26 (m, 1H), 6.78–6.94 (m, 4H, aromatic protons), 7.04–7.30 (m, 6H, aromatic protons).

EXAMPLE 3

23 mg (0.058 mmol) of (2R,4S,5S)-3-t-butoxycarbonyl-2-(4-methoxyphenyl)-4-phenyl-1,3-oxazolidine-5-carboxylic acid in 1 cm³ of anhydrous toluene are introduced, under an argon atmosphere, into a 5 cm³ single-necked, round-bottomed flask equipped with a magnetic stirrer system and then 11.9 mg (0.058 mmol) of dicyclohexylcarbodiimide are added. The mixture is allowed to react for 5 minutes at a temperature in the region of 25° C. and then a mixture of 2.3 mg (0.019 mmol) of 4-(N,N-dimethylamino)pyridine and 17 mg (0.019 mmol) of 4-acetoxy-2α-benzoyloxy-5β,20-epoxy-1,13α-dihydroxy-9-oxo-7β,10β-bis(2,2,2-trichloroethoxy-carbonyloxy)-11-taxene is added. The mixture is allowed to react for 5 minutes at 25° C. and is then heated for 24 hours at 74° C. After evaporation of the toluene under reduced pressure, the residue obtained (74 mg) is purified by silica gel thin layer chromatography, eluting with an ethyl ether/dichloromethane (5/95 by volume) mixture. There are thus obtained 23.4 mg (0.012 mmol) of 4-acetoxy-2α-benzoyloxy-5β,20-epoxy-1-hydroxy-9-oxo-7β,10β-bis(2,2,2-trichloroethoxycarbonyl)oxy-11-taxen-13α-yl (2R,4S,5R)-3-t-butoxycarbonyl-2-(4-methoxyphenyl)-4-phenyl-1,3-oxazolidine-5-carboxylate contaminated with 15% of 4-acetoxy-2α-benzoyloxy-5β,20-epoxy-1-hydroxy-9-oxo-7β,10β-bis(2,2,2-trichloroethoxycarbonyl)oxy-11-taxen-13α-yl (2R,4S,5S)-3-t-butoxycarbonyl-2-(4-methoxyphenyl)-4-phenyl-1,3-oxazolidine-5-carboxylate.

4-Acetoxy-2α-benzoyloxy-5β,20-epoxy-1-hydroxy-9-oxo-7β,10β-bis(2,2,2-trichloroethoxy-carbonyl)oxy-11-taxen-13α-yl (2R,4S,5R)-3-t-butoxycarbonyl-2-(4-methoxyphenyl)-4-phenyl-1,3-oxazolidine-5-carboxylate has the following characteristics:

melting point: 164°–167° C.

infrared spectrum (film): main characteristic absorption bands at 3500, 2950, 2900, 1760, 1730, 1720, 1700, 1605, 1580, 1505, 1380, 1375, 1360, 1240, 1140, 1060, 815, 760 and 710 cm$^{-1}$ proton nuclear magnetic resonance spectrum (500 MHz, CDCl$_3$, chemical shifts in ppm, coupling constants J in Hz): 1.05 (s, 9H), 1.16 (s, 3H), 1.24 (s, 3H), 1.64 (s, 3H), 1.80 (s, 3H), 1.85 (broad s, 3H), 1.98–2.05 (m, 1H), 2.07–2.14 (m, 1H), 2.18–2.26 (m, 1H), 2.53–2.64 (m, 1H), 3.81 (d, J=7.0, 1H), 3.82 (s, 3H), 4.18 (AB$_q$, J$_{AB}$=8.5, δ$_A$–δ$_B$=80.7, 2H), 4.58 (s, 1H), 4.74 (AB$_q$, J$_{AB}$=11.8, δ$_A$–δ$_B$=150.6, 2H), 4.77 (AB$_q$, J$_{AB}$=11.8, δ$_A$–δ$_B$=7.7, 2H), 4.88 (distorted d, J=9.3, 1H), 5.41 (broad s, 1H), 5.50 (dd, J=7.2 and 10.7, 1H), 5.64 (d, J=7.0, 1H), 6.10 (t, J=8.8, 1H), 6.14 (s, 1H), 6.40 (broad s, 1H), 6.93 (d, J=8.8, 2H, aromatic protons), 7.26–7.44 (m, 7H, aromatic protons), 7.48–7.52 (m, 2H, aromatic protons), 7.62–7.65 (m, 1H, aromatic proton), 8.01–8.03 (m, 2H, aromatic protons).

13 mg (0.01 mmol) of the ester obtained above (mixture of the 2 epimers), in solution in 0.75 cm³ of methanol, are introduced into a 5 cm³ single-necked flask equipped with a magnetic stirrer system and then 0.75 cm³ of glacial acetic acid is added. The mixture is heated at 65° C. for 5 minutes and then 65 mg of zinc/copper couple (prepared from 20 g of zinc and 3 g of copper sulphate monohydrate) are added. The black heterogeneous mixture is stirred at 65° C. for 30 minutes. After cooling to a temperature in the region of 25° C., the reaction mixture is diluted in 30 cm³ of dichloromethane. Filtration is carried out through Celite and then the solids are washed 3 times with 10 cm³ of dichloromethane. The solvents are removed under reduced pressure. The residue obtained is purified by silica gel thin layer chromatography, eluting with a methanol/dichloromethane (5/95 by volume) mixture. There are thus obtained, with a yield of 60%, 5.6 mg (0.006 mmol) of 4-acetoxy-2α-benzoyloxy-5β,20-epoxy-9-oxo-1,7β,10β-trihydroxy-11-taxen-13α-yl (2R,4S,5R)-3-t-butoxycarbonyl-2-(4-methoxyphenyl)-4-phenyl-1,3-oxazolidine-5-carboxylate contaminated with 15–20% of 4-acetoxy-2α-benzoyloxy-5β,20-epoxy-9-oxo-1,7β,10β-trihydroxy-11-taxen-13α-yl (2R,4S,5S)-3-t-butoxycarbonyl-2-(4-methoxyphenyl)-4-phenyl-1,3-oxazolidine-5-carboxylate.

4-Acetoxy-2α-benzoyloxy-5α,20-epoxy-9-oxo-1,7β,10β-trihydroxy-11-taxen-13α-yl (2R,4S,5R)-3-t-butoxycarbonyl-2-(4-methoxyphenyl)-4-phenyl-1,3-oxazolidine-5-carboxylate has the following characteristics:

infrared spectrum (film): characteristic absorption bands at 3430, 2960, 2880, 2840, 1730, 1720, 1700, 1685, 1605, 1580, 1505, 1440, 1380, 1360, 1340, 1265, 1240, 1170, 1130, 1060, 1015, 975, 905, 720 and 695 cm$^{-1}$ proton nuclear magnetic resonance spectrum (400 MHz, CDCl$_3$, chemical shifts in ppm, coupling constants J in Hz): 1.05 (s, 9H), 1.09 (s, 3H), 1.20 (s, 3H), 1.57 (s, 3H), 1.70 (s, 3H), 1.73–1.90 (m, 1H), 1.85 (broad s, 3H), 2.02–2.19 (m, 2H), 2.47–2.60 (m, 1H), 3.81 (d, J=7, 1H), 3.82 (s, 3H), 4.15 (d, J=1.5, 1H), 4.18 (AB$_q$, J$_{AB}$=8.5, δ$_A$–δ$_B$=55.6, 2H), 4.56 (d, J=5.0, 1H), 4.87 (dis. dd, J=8, 1H), 5.10 (d, J=1.5, 1H), 5.42 (broad s, 1H), 5.62 (d, J=4, 1H), 6.13 (t, J=8, 1H), 6.39 (broad s, 1H), 6.92 (m, 2H, aromatic protons), 7.30–7.44 (m, 7H, aromatic protons), 7.47–7.51 (m, 2H, aromatic protons), 7.59–7.64 (m, 1H, aromatic proton), 8.01–8.05 (m, 2H, aromatic protons)

mass spectrum (FAB(+)-NBA matrix+KCl): 1276 (M$^{30}$)

| | | | |
|---|---|---|---|
| calculated | C % 53.62 | H % 4.81 | N % 1.10 |
| found | 53.22 | 4.82 | 1.16 |

4.4 mg (0.0047 mmol) of the product obtained above are introduced into a 5 cm$^3$ single-necked flask equipped with a magnetic stirrer. The mixture is cooled to 0° C. and then 64 μl of an ethyl acetate solution containing 0.28 μl of 33% hydrochloric acid are added. The resulting homogeneous reaction mixture is allowed to react for 5 minutes at 0° C. and then for 5 hours at a temperature in the region of 25° C. The reaction mixture is diluted in 20 cm$^3$ of ethyl acetate and then the organic phase is treated with 5 cm$^3$ of a saturated aqueous sodium bicarbonate solution. The organic phase, separated by settling, is washed with 3 times 5 cm$^3$ of water and once with 5 cm$^3$ of a saturated aqueous sodium chloride solution and is then dried over anhydrous sodium sulphate. After filtration and concentration to dryness under reduced pressure, the residue obtained is purified by silica gel thin layer chromatography, eluting with a methanol/dichloromethane (5/95 by volume) mixture. There are thus obtained, with a yield of 78%, 3.0 mg (0.0037 mmol) of pure 4-acetoxy-2α-benzoyloxy-5β,20-epoxy-9-oxo-1,7β,10β-trihydroxy-11-taxen-13α-yl (2R,3S)-3-t-butoxycarbonylamino-3-phenyl-2-hydroxypropionate (or Taxotere) which contains no trace of 4-acetoxy-2α-benzoyloxy-5β, 20-epoxy-9-oxo-1,7β, 10β-trihydroxy-11-taxen-13α-yl (2S,3S)-3-t-butoxycarbonylamino-3-phenyl-2-hydroxypropionate.

There is recovered 0.8 mg (0.0009 mmol) of 4-acetoxy-2α-benzoyloxy-5β, 20-epoxy-9-oxo-1,7β, 10β-trihydroxy-11-taxen-13α-yl (2R,4S,5S)-3-t-butoxycarbonyl-2-(4-methoxyphenyl)-4-phenyl-1,3-oxazolidine-5-carboxylate which is not deprotected under the conditions used.

The Taxotere thus obtained has the following characteristics:

infrared spectrum (film): main characteristic absorption bands at 3450, 3100, 3050, 2950, 2920, 2890, 2850, 1730, 1710, 1600, 1580, 1490, 1450, 1390, 1370, 1315, 1270, 1245, 1160, 1105, 1095, 1070, 1020, 980, 910, 730 and 710 cm$^{-1}$ proton nuclear magnetic resonance spectrum (300 MHz, CDCl$_3$, chemical shifts in ppm, coupling constants J in Hz): 1.13 (s, 3H), 1.24 (s, 3H), 1.34 (s, 9H), 1.76 (s, 3H), 1.85 (s, 3H), 1.74–1.85 (m, 1H), 2.26–2.29 (m, 2H), 2.37 (s, 3H), 2.54–2.66 (m, 1H), 3.31 (distorted d, J=4.4, 1H), 3.92 (d, J=7, 1H), 4.18–4.30 (m, 1H), 4.18 (s, 1H), 4.25 (AB$_q$, J$_{AB}$=8.3, δ$_A$–δ$_B$=35.3, 2H), 4.62 (broad s, 1H), 4.94 (d, J=8.5, 1H), 5.20 (s, 1H), 5.26 (broad distorted s, 1H), 5.41 (distorted d, J=9.4, 1H), 5.68 (d, J=7, 1H), 6.21 (t, J=8.0 and 8.8, 1H), 7.31–7.40 (m, 5H, aromatic protons), 7.47–7.52 (m, 2H, aromatic protons), 7.59–7.64 (m, 1H, aromatic proton), 8.09–8.12 (m, 2H, aromatic protons).

(2R,4S,5S)-3-t-Butoxycarbonyl-2-(4-methoxyphenyl)-4-phenyl-1,3-oxazolidine-5-carboxylic acid can be prepared in the following way:

33 mg (0.08 mmol) of (2R,4S,5S)-3-t-butoxycarbonyl-2-(4-methoxyphenyl)-4-phenyl-5-methoxycarbonyl-1,3-oxazolidine, in suspension in 15 cm$^3$ of methanol, are put, under an argon atmosphere, into a 50 cm$^3$ round-bottomed flask equipped with a magnetic stirrer system. 5 cm$^3$ of water and 33 mg (0.24 mmol) of potassium carbonate are then added. The mixture is allowed to react for 96 hours at a temperature in the region of 25° C. The reaction mixture becomes homogeneous. The methanol is removed under reduced pressure. The basic aqueous phase is diluted in 10 cm$^3$ of water and then extracted with 3 times 15 cm$^3$ of ether. The aqueous phase is cooled to 0° C. and is then acidified, with vigorous stirring in the presence of 20 cm$^3$ of dichloromethane, with a 4M aqueous hydrochloric acid solution to a pH of less than 1. The acidic aqueous phase is extracted 8 times with 20 cm$^3$ dichloromethane. The combined organic phases are washed with 3 times 5 cm$^3$ of water and then once with 5 cm$^3$ of a saturated aqueous sodium chloride solution. The organic phases are dried over anhydrous sodium sulphate. After filtration and concentration to dryness under reduced pressure, there are obtained, with a yield of 94%, 30.0 mg (0.075 mmol) of (2R,4S,5S)-3-t-butoxycarbonyl-2-(4-methoxyphenyl)-4-phenyl-1,3-oxazolidine-5-carboxylic acid, the characteristics of which are the following:

melting point: 148.5°–150.5° C.

optical rotation: [α]$_D^{25}$=+46.4° (c =1.0, chloroform)

infrared spectrum (film): main characteristic absorption bands at 3700–2300, 2950, 2900, 2820, 1755, 1700, 1605, 1580, 1505, 1385, 1360, 1300, 1285, 1240, 1215, 1165, 1130, 1075, 1065, 1020, 930, 900, 850, 820 and 685 cm$^{-1}$ proton nuclear magnetic resonance spectrum in the form of 2 rotamers (200 MHz, CDCl$_3$), chemical shifts in ppm, coupling constants J in Hz): 1.11 (s, 9H), 3.82 (s, 3H), 4.2 (very broad s, 1H), 4.99 (d, J=6.4, 1H), 5.18 (majo distorted d, J=6.4) and 5.36 (mino, broad s) (1H), 6.46 (mino) and 6.66 (majo) (s, 2H), 6.94 J=8.6, 2H, aromatic protons), 7.20–7.46 (m, 7H, aromatic protons).

mass spectrum (C.I., NH$_3$+isobutane): 417 (MH$^+$+NH$_3$), 400 (MH$^+$), 361, 344, 300, 264, 225, 192, 177, 137.

(2R,4S,5S)-3-t-Butoxycarbonyl-2-(4-methoxyphenyl)-4-phenyl-5-methoxycarbonyl-1,3-oxazolidine can be prepared according to one of the following methods:

1) 10 mg (0.034 mmol) of methyl (2S,3S)-3-t-butoxycarbonyl-3-phenyl-2-hydroxypropionate, in suspension in 0.5 cm$^3$ of anhydrous toluene, are put, under an argon atmosphere, into a 2 cm$^3$ single-necked, round-bottomed flask equipped with a magnetic stirrer system. 1 mg (0.004 mmol) of pyridinium p-toluenesulphonate is then added. The resulting reaction mixture is heated to 115° C. After 5 minutes at this temperature, 13μl (13.9 mg, 0.076 mmol) of p-methoxybenzaldehyde dimethyl acetal are added. The reaction mixture, which has become homogeneous, is heated at reflux of the solvent for 5 minutes. After cooling to a temperature in the region of 20° C., the reaction mixture is diluted in 30 cm$^3$ of dichloromethane. The organic phase is treated once with 5 cm$^3$ of a saturated aqueous sodium bicarbonate solution and then washed with 2 times 5 cm$^3$ of water and once with 5 cm$^3$ of a saturated aqueous sodium chloride solution. After drying over anhydrous sodium sulphate, filtration and concentration to dryness under reduced pressure, the residue is purified by silica gel thin layer chromatography, eluting with an ethyl ether/hexane (6/4 by volume) mixture. There are thus obtained 13.9 mg (0.0336 mmol) of a mixture of (2R,4S,5S)-3-t-butoxycarbonyl-2-(4-methoxyphenyl)-4-phenyl-5-methoxycarbonyl-1,3-oxazolidine and (2S,4S,5S)-3-t-butoxycarbonyl-2-(4-methoxyphenyl)-4-phenyl-5-methoxycarbonyl-1,3-oxazolidine in the ratio 40/60. The overall yield is 99%.

These esters can be separated by chromatography on a column of silica gel, eluting with an ethyl ether/hexane (2/8 by volume) mixture.

(2R,4S,5S)-3-t-Butoxycarbonyl-2-(4-methoxy-phenyl)-4-phenyl-5-methoxycarbonyl-1,3-oxazolidine has the following characteristics:

melting point: 208°–208.5° C.

optical rotation $[\alpha]_D^{25}=+53°$ (c=1.1, chloroform)

infrared spectrum (film): 2950, 1725, 1680, 1600, 1575, 1500, 1380, 1350, 1280, 1260, 1240, 1200, 1160, 1120, 1065, 1050, 1030 and 1010 cm$^{-1}$ proton nuclear magnetic resonance spectrum in the form of 2 rotamers (200 MHz, CDCl$_3$, chemical shifts in ppm, coupling constants J in Hz): 1.12 (s, 9H), 3.32 (s, 3H), 3.82 (s, 3H), 5.00 (d, J=6.5, 1H), 5.16 (majo, distorted d, J=5.6) and 5.34 (mino, broad s, 1H), 6.48 (mino) and 6.68 (majo) (2s, 1H), 6.93 (d, J=8.4, 2H, aromatic protons), 7.20–7.50 (m, 7H, aromatic protons)

mass spectrum (D/CI, NH$_3$+isobutane): 414 (MH$^+$), 356, 314, 312, 250, 222, 206, 179, 177, 162, 151, 134, 119.

(2S,4S,5S)-3-t-Butoxycarbonyl-2-(4-methoxyphenyl)-4-phenyl-5-methoxycarbonyl-1,3-oxazolidine has the following characteristics.

infrared spectrum (film): main characteristic absorption bands at 2950, 2900, 1760, 1730, 1695, 1600, 1580, 1505, 1450, 1430, 1380, 1360, 1335, 1290, 1240, 1210, 1160, 1150, 1080, 1030, 1020, 920, 801 and 680 cm$^{-1}$ proton nuclear magnetic resonance spectrum (200 MHz, CDCl3, chemical shifts in ppm, coupling constants J in Hz)=1.26 (s, 9H), 3.37 (s, 3H), 3.82 (s, 3H), 5.01 (d, J=7.1, 1H), 5.27 (d, J=7.1, 1H), 6.05 (s, 1H), 6.91 (d, J=8.4, 2H, aromatic protons), 7.26–7.56 (m, 5H, aromatic protons), 7.49 (d, J=8.4, 2H, aromatic protons)

mass spectrum (D/CI, NH$_3$+isobutane): 414 (MH$^+$), 356, 339, 314, 312, 296, 250, 224, 222, 206, 177, 162, 151, 135, 121.

2) 5.0 mg (0.017 mmol) of methyl (2S,3S)-3-t-butoxycarbonylamino-3-phenyl-2-hydroxypropionate, in suspension in 0.25 cm$^3$ of anhydrous toluene, are put, under an argon atmosphere, in a 2 cm$^3$ round-bottomed flask equipped with a magnetic stirrer system. 10.0 μl (10.7 mg, 0.059 mmol) of p-methoxybenzaldehyde dimethyl acetal are then added. The resulting reaction mixture is heated to 95° C. and then 1 mg of pyridinium-polymer p-toluenesulphonate is added. Heating is continued for 24 hours at 95° C. After cooling to a temperature in the region of 20° C., the reaction mixture is diluted in 30 cm$^3$ of dichloromethane. The organic phase is treated once with 5 cm$^3$ of a saturated aqueous sodium bicarbonate solution, then washed with 3 times with 5 cm$^3$ of water and once with 5 cm$^3$ of a saturated aqueous sodium chloride solution. After drying over anhydrous sodium sulphate, filtration and concentration to dryness, there are obtained, after purification by silica gel thin layer chromatography, eluting with an ethyl ether/hexane (1/1 by volume, 2 passes) mixture, with a yield of 93%, 6.5 mg (0.016 mmol) of a mixture of (2R,4S,5S)-3-t-butoxycarbonyl-2-(4-methoxyphenyl)-4-phenyl-5-methoxycarbonyl-1,3-oxazolidine and (2S,4S,5S)-3-t-butoxycarbonyl-2-(4-methoxyphenyl)-4-phenyl-5-methoxycarbonyl-1,3-oxazolidine in the ratio 30/70.

3) 10.0 mg (0.034 mmol) of methyl (2S,3S)-3-t-butoxycarbonylamino-3-phenyl-2-hydroxypropionate, in suspension in 0.5 cm$^3$ of anhydrous toluene, are put, under an argon atmosphere, in a 2 cm$^3$ single-necked, round-bottomed flask equipped with a magnetic stirrer system. 13.0 μl (13.9 mg, 0.076 mmol) of p-methoxybenzaldehyde dimethyl acetal are then added. The resulting reaction mixture is heated at 74° C. for 5 minutes and then 2.5 mg of p-toluenesulphonic acid monohydrate are added. Heating is continued at 74° C. for 17 hours. After cooling, the reaction mixture is diluted in 30 cm$^3$ dichloromethane. The organic phase is treated once with 5 cm$^3$ of a saturated aqueous sodium bicarbonate solution, then washed 2 times with 5 cm$^3$ of water and once with 5 cm$^3$ of a saturated aqueous sodium chloride solution. After drying over anhydrous sodium sulphate, filtration and concentration to dryness under reduced pressure, there are obtained, after purification by silica gel thin layer chromatography, eluting with an ethyl ether/hexane (1/1 by volume) mixture, with yield of 45%, 6.3 mg (0.015 mmol) of a mixture of (2R,4S,5S)-3-t-butoxycarbonyl-2-(4-methoxyphenyl)-4-phenyl-5-methoxycarbonyl-1,3-oxazolidine and (2S,4S,5S)-3-t-butoxycarbonyl-2-(4-methoxyphenyl)-4-phenyl-5-methoxycarbonyl-1,3-oxazolidine in the ratio 61/39.

4) 5.0 mg (0.017 mmol) of methyl (2S,3S)-3-t-butoxycarbonylamino-3-phenyl-2-hydroxypropionate, in suspension in 0.25 cm$^3$ of anhydrous toluene, are put, under an argon atmosphere, in a 2 cm$^3$ single-necked, round-bottomed flask equipped with a magnetic stirrer system. 6.5 μl (6.95 mg, 0.038 mmol) of p-methoxybenzaldehyde dimethyl acetal are then added. The resulting reaction mixture is heated at 76° C. for 5 minutes and then 0.5 mg (0.002 mmol) of camphorsulphonic acid is added. Heating is continued at 76° C. After reacting for 4 hours, 4.0 μl (2.43 mg, 0.076 mmol) of methanol are added and the mixture is allowed to react for a further 44 hours at 76° C. After cooling, the reaction mixture is diluted in 30 cm$^3$ of dichloromethane. The organic phase is treated once with 5 cm$^3$ of a saturated aqueous sodium bicarbonate solution, then washed 2 times with 5 cm$^3$ of water and once with 5 cm$^3$ of a saturated aqueous sodium chloride solution. After drying over anhydrous sodium sulphate, filtration and concentration to dryness under reduced pressure, there are obtained, after purification by silica gel thin layer chromatography, eluting with an ethyl ether/hexane (3/2 by volume) mixture, with a yield of 53%, 3.7 mg (0.009 mmol) of a mixture of (2R,4S,5S)-3-t-butoxycarbonyl-2-(4-methoxyphenyl)-4-phenyl-5-methoxycarbonyl-1,3-oxazolidine and (2S,4S,5S)-3-t-butoxycarbonyl-2-(4-methoxyphenyl)-4-phenyl-5-methoxycarbonyl-1,3-oxazolidine in the ratio 74/26.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for preparing a taxane derivative of formula I:

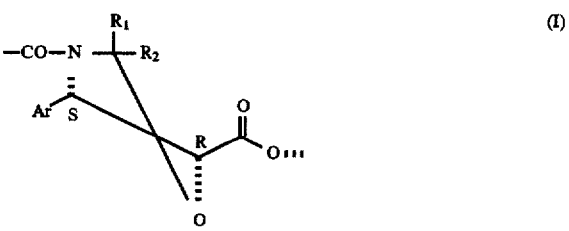

-continued

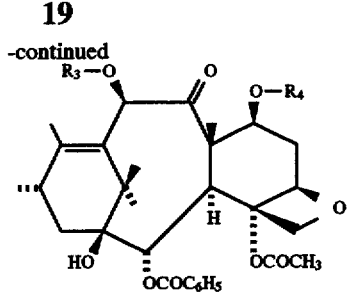

in which:

Ar represents an aryl radical;

R represents a phenyl radical or a radical $R_5$—O— in which $R_5$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms, or a bicycloalkyl radical containing 7 to 11 carbon atoms, these radicals being unsubstituted or substituted by at least one substituent selected from a halogen atom and a hydroxyl radical, an alkoxy radical containing 1 to 4 carbon atoms, a dialkylamino radical in which each alkyl portion contains 1 to 4 carbon atoms, a piperidino radical, a morpholino radical, a 1-piperazinyl radical (unsubstituted or substituted in the 4-position by an alkyl radical containing 1 to 4 carbon atoms or by a phenylalkyl radical in which the alkyl portion contains 1 to 4 carbon atoms), a cycloalkyl radical containing 3 to 6 carbon atoms, a cycloalkenyl radical containing 4 to 6 carbon atoms, a phenyl radical, a cyano radical, a carboxyl radical, and an alkoxycarbonyl radical in which the alkyl portion contains 1 to 4 carbon atoms, wherein the cycloalkyl, cycloalkenyl or bicycloalkyl radicals are unsubstituted or substituted by at least one alkyl radical comprising 1 to 4 carbon atoms;

a phenyl radical unsubstituted or substituted by at least one substituent selected from a halogen atom, an alkyl radical containing 1 to 4 carbon atoms, and an alkoxy radical containing 1 to 4 carbon atoms; or a saturated or unsaturated nitrogen containing heterocyclic radical containing 4 to 6 members and unsubstituted or substituted by one alkyl radical containing 1 to 4 carbon atoms;

$R_1$ and $R_2$, which are identical or different, represent a hydrogen atom or an alkyl, phenylalkyl, phenyl, alkoxyphenyl, or dialkoxyphenyl radical, or else $R_1$ and $R_2$ form, together with the carbon atom to which they are bonded, a ring having from 4 to 7 members;

$R_3$ represents an acetyl radical or a protecting group of the hydroxyl functional group; and $R_4$ represents a protecting group of the hydroxyl functional group; the process comprising esterifying a protected baccatin III or protected 10-deacetylbaccatin III of formula (II):

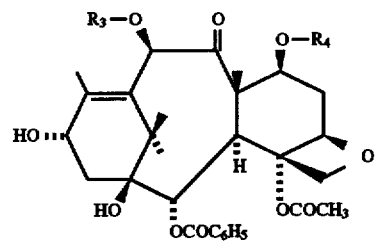

in which $R_3$ and $R_4$ are defined as above, with an acid of formula (VI):

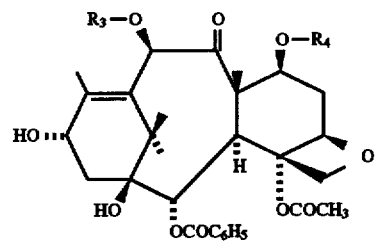

in which Ar, R, $R_1$ and $R_2$ are defined as above, or with an anhydride or with an activated derivative of this acid.

2. The process according to claim 1, wherein the esterification is carried out with an acid of formula (VI):

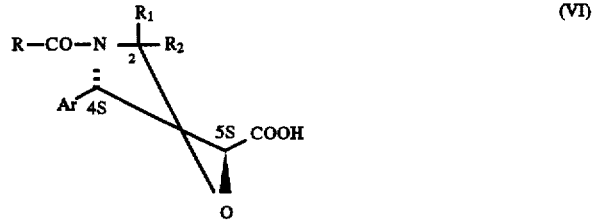

in which Ar, R, $R_1$ and $R_2$ are defined as in claim 17, the reaction being carried out in the presence of a condensation agent and an activating agent in an organic solvent at a temperature between 0° and 90° C.

3. The process according to claim 2, wherein the condensation agent is selected from imides and reactive carbonates and the activating agent is selected from aminopyridines.

4. The process according to claim 3, wherein the condensation agent is selected from dicyclohexylcarbodiimide and di-2-pyridyl ketone and the activating agent is selected from 4-dimethylaminopyridine and 4-pyrrolidinopyridine.

5. The process according to claim 2, wherein the solvent is selected from ethers, ketones, esters, nitriles, aliphatic hydrocarbons, halogenated aliphatic hydrocarbons and aromatic hydrocarbons.

6. The process according to claim 5, wherein the solvent is selected from aromatic hydrocarbons.

7. The process according to claim 1, wherein the esterification is carried out with an anhydride of formula (VII):

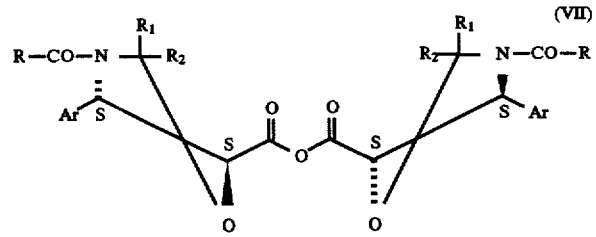

in which Ar, R, $R_1$ and $R_2$ are defined as in claim 1, the reaction being carried out in the presence of an activating agent in an organic solvent at a temperature between 0° and 90° C.

8. The process according to claim 7, wherein the activating agent is selected from aminopyridines.

9. The process according to claim 8, wherein the activating agent is selected from 4-dimethylaminopyridine and 4-pyrrolidinopyridine.

10. The process according to claim 7, wherein the solvent is selected from ethers, ketones, esters, nitriles, aliphatic hydrocarbons, halogenated aliphatic hydrocarbons and aromatic hydrocarbons.

11. The process according to claim 1, wherein the esterification is carried out with an activated acid of formula (VIII):

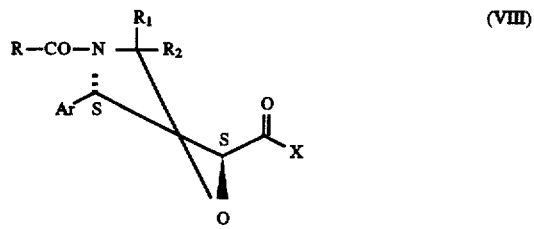

(VIII)

in which Ar, R, $R_1$ and $R^2$ are defined as in claim 1, and X represents a halogen atom or an acyloxy or aroyloxy radical, optionally prepared in situ in the presence of a base, the reaction being carried out in an organic solvent at a temperature between 0° and 90° C.

12. The process according to claim 11, wherein the base is selected from nitrogenous organic bases.

13. The process according to claim 12, wherein the nitrogenous organic base is selected from aliphatic tertiary amines, pyridine and aminopyridines.

14. The process according to claim 11, wherein the organic solvent is selected from ethers, ketones, esters, nitriles, aliphatic hydrocarbons, halogenated aliphatic hydrocarbons and aromatic hydrocarbons.

15. The process according to claim 14, wherein the solvent is selected from aromatic hydrocarbons.

* * * * *

UNITED STATES PATENT AND TRADEMARK OFFICE
CERTIFICATE OF CORRECTION

PATENT NO. : 5,686,623
DATED : November 11, 1997
INVENTOR(S) : Jean-Noel DENIS et al.

It is certified that error appears in the above-identified patent and that said Letters Patent is hereby corrected as shown below:

In the Claims:

Claim 1, column 19, line 52, "nitrogen containing" should read --nitrogen-containing--.

Claim 11, column 22, line 1, "$R^2$" should read --$R_2$--.

Signed and Sealed this

Tenth Day of November 1998

Attest:

BRUCE LEHMAN

Attesting Officer

Commissioner of Patents and Trademarks